(12) United States Patent
Greber

(10) Patent No.: US 12,150,657 B2
(45) Date of Patent: Nov. 26, 2024

(54) TENSOR DEVICE FOR REVISION KNEE ARTHROPLASTY

(71) Applicant: Zimmer, Inc., Warsaw, IN (US)

(72) Inventor: Eric Greber, Thibodaux, LA (US)

(73) Assignee: Zimmer, Inc., Warsaw, IN (US)

( * ) Notice: Subject to any disclaimer, the term of this patent is extended or adjusted under 35 U.S.C. 154(b) by 126 days.

(21) Appl. No.: 17/540,414

(22) Filed: Dec. 2, 2021

(65) Prior Publication Data

US 2022/0175400 A1    Jun. 9, 2022

Related U.S. Application Data

(60) Provisional application No. 63/120,888, filed on Dec. 3, 2020.

(51) Int. Cl.
| | |
|---|---|
| *A61B 17/02* | (2006.01) |
| *A61B 17/16* | (2006.01) |
| *A61B 17/17* | (2006.01) |
| *A61B 34/00* | (2016.01) |
| *A61B 34/10* | (2016.01) |
| *A61B 34/30* | (2016.01) |

(52) U.S. Cl.
CPC ........ *A61B 17/1764* (2013.01); *A61B 17/164* (2013.01); *A61B 34/10* (2016.02); *A61B 34/25* (2016.02); *A61B 34/30* (2016.02); *A61B 2034/104* (2016.02)

(58) Field of Classification Search
CPC . A61B 17/155; A61B 17/164; A61B 17/1764; A61B 2017/0268; A61B 2090/061; A61F 2/4657
See application file for complete search history.

(56) References Cited

U.S. PATENT DOCUMENTS

| | | | |
|---|---|---|---|
| 7,715,602 B2 | 5/2010 | Richard | |
| 2010/0241126 A1* | 9/2010 | Ghijselings | A61B 17/155 606/88 |
| 2014/0288563 A1* | 9/2014 | Claypool | A61B 17/155 606/88 |
| 2022/0008136 A1* | 1/2022 | Cameron | A61B 34/20 |

* cited by examiner

*Primary Examiner* — Samuel S Hanna
(74) *Attorney, Agent, or Firm* — SCHWEGMAN LUNDBERG & WOESSNER, P.A.

(57) ABSTRACT

Systems and methods may use a tensor device in various aspects of a knee revision. For example, the tensor device may include a femoral arm configured to couple with an end portion of a femoral intramedullary canal reamer and a tibial arm moveably connected to the femoral arm, the tibial arm configured to couple with an end portion of a tibial intramedullary canal reamer. The tensor device may include a component or be used to identify a knee gap or a component size for an implant.

4 Claims, 14 Drawing Sheets

```
                                                    ┌─ 500
                                   ┌─ 502
┌─────────────────────────────────────────────────────────────┐
│  RECEIVE AN INDICATION INCLUDING A JOINT LINE OF A KNEE FOR A REVISION  │
│                           PROCEDURE                         │
└─────────────────────────────────────────────────────────────┘
                              │
                              ▼          ┌─ 504
┌─────────────────────────────────────────────────────────────┐
│  CAUSE A ROBOTIC ARM TO ALIGN A FEMORAL ARM OF A TENSOR DEVICE  │
│ PARALLEL TO AN INTRAMEDULLARY AXIS OF A TIBIA WHILE A TIBIAL ARM OF THE │
│   TENSOR DEVICE IS CONNECTED TO A HANDLE PORTION OF A TIBIAL REAMER    │
└─────────────────────────────────────────────────────────────┘
                              │
                              ▼          ┌─ 506
┌─────────────────────────────────────────────────────────────┐
│  DETERMINE A COMPONENT SIZE FOR AN IMPLANT OR A KNEE GAP BASED ON │
│              THE ALIGNMENT OF THE FEMORAL ARM                │
└─────────────────────────────────────────────────────────────┘
                              │
                              ▼          ┌─ 508
┌─────────────────────────────────────────────────────────────┐
│  OUTPUT THE COMPONENT SIZE OR THE KNEE GAP FOR DISPLAY IN A USER │
│                          INTERFACE                          │
└─────────────────────────────────────────────────────────────┘
```

*FIG. 5*

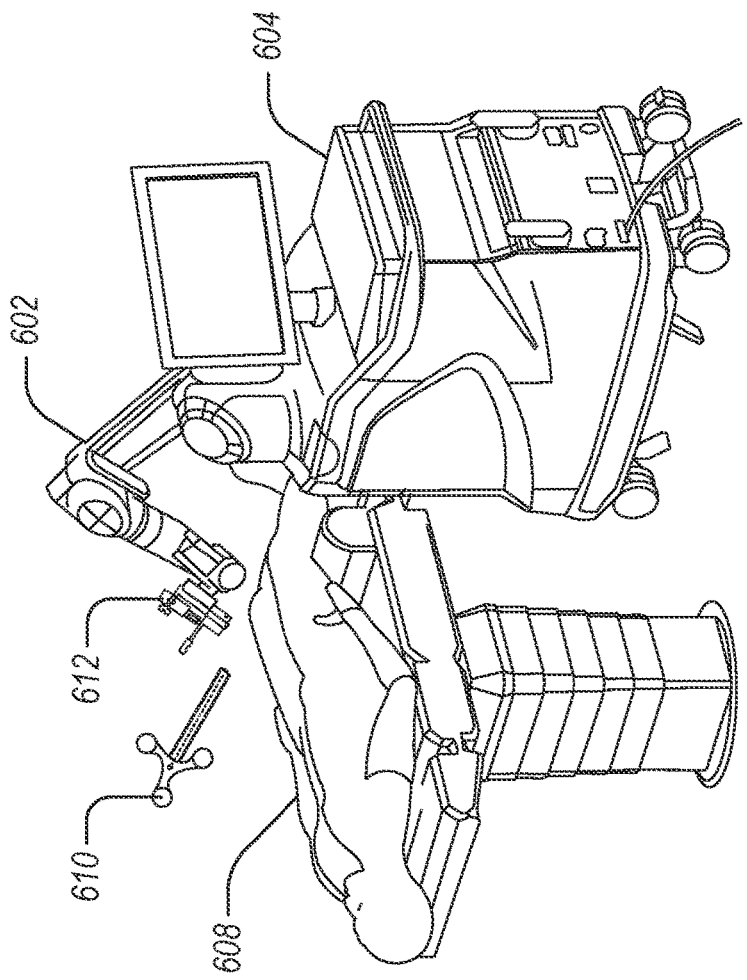
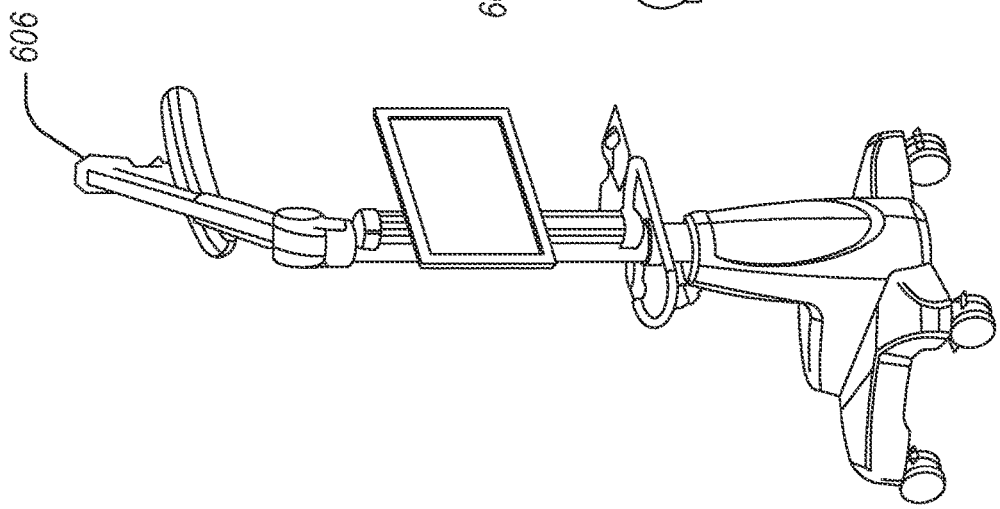
FIG. 6

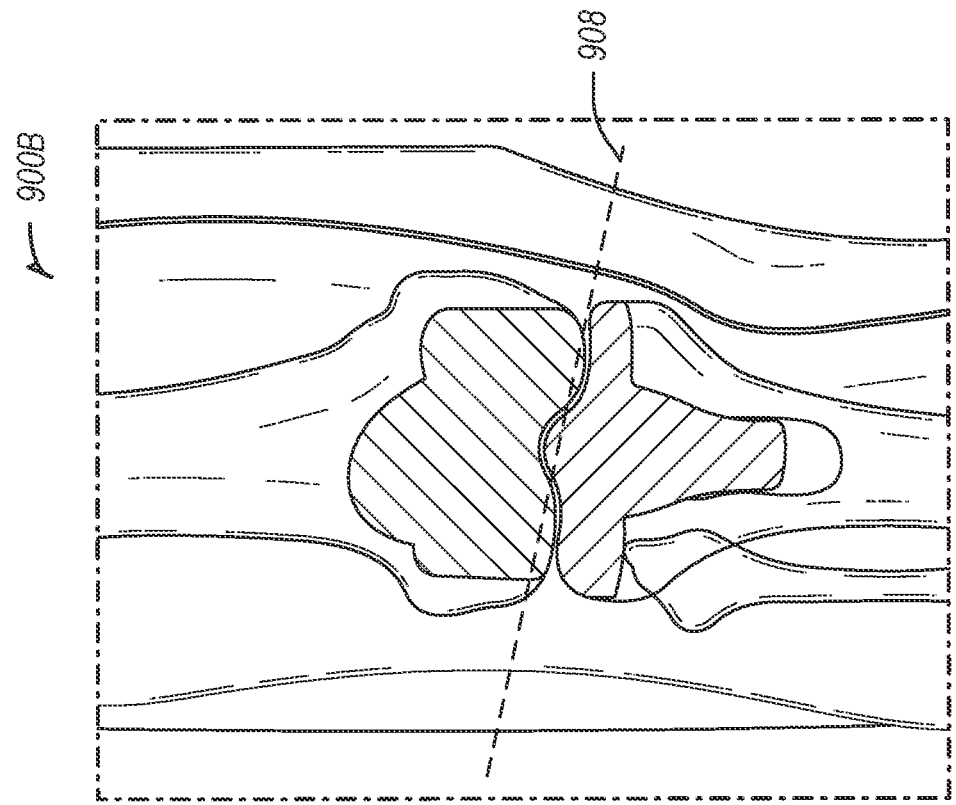
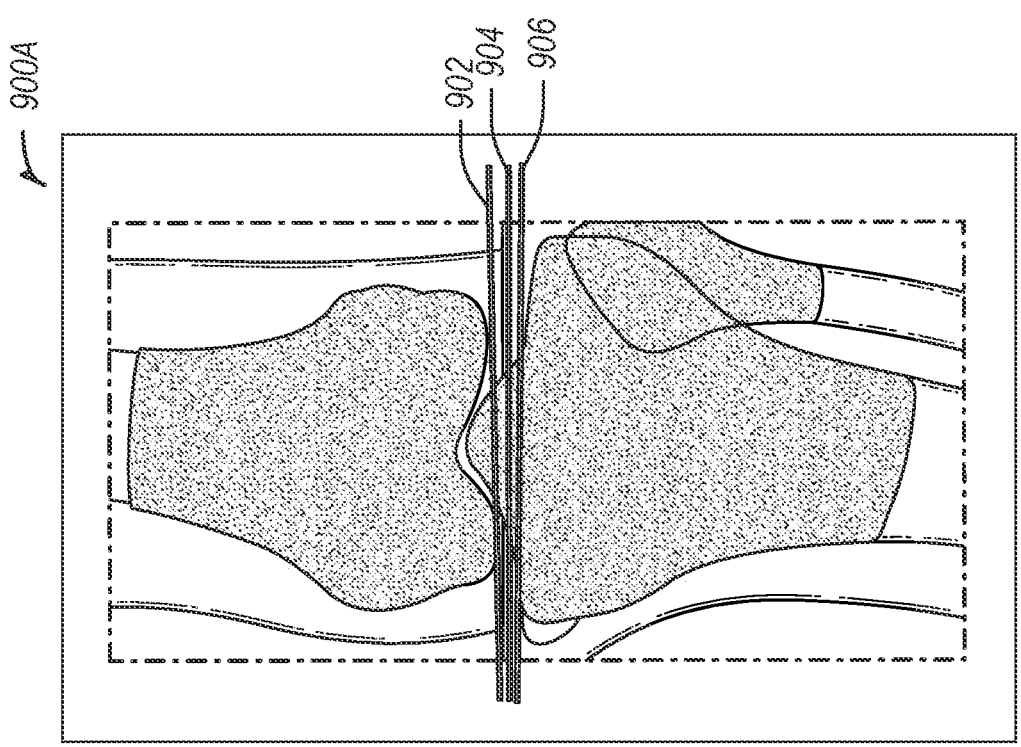
FIG. 9B
FIG. 9A

TENSOR DEVICE FOR REVISION KNEE ARTHROPLASTY

CLAIM OF PRIORITY

This application claims the benefit of priority to U.S. Provisional Application No. 63/120,888 filed Dec. 3, 2020, titled "TENSOR DEVICE FOR REVISION KNEE ARTHROPLASTY," which is hereby incorporated herein by reference in its entirety.

BACKGROUND

An implant revision surgery is a process by which an existing implant is removed to be replaced by a new implant. However, due to the bond between the implant to be removed and the bone or from the damage of a loose implant, osteolysis, or infection, the bone is often damaged after implants have been removed. As a result, the subsequent positioning and installation of a replacement implant may lack precision due to damaged bone surfaces and abnormal ligament tension. For instance, in knee revision surgery, machining of the bone surfaces using conventional cutting blocks may lack precision as conventional bone landmarks used for defining the orientation of the cutting block may be altered or removed during the removal of the implant.

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. Many conventional orthopedic joint repair or replacement surgery techniques may result in errors or may lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 illustrates a flowchart showing a technique for using a tensor device in accordance with at least one example of this disclosure.

FIG. 6 illustrates a robotic surgical system including a robotic surgical device (e.g., a robot or a robotic arm) and a computer (e.g., a device having a processor) in accordance with at least one example of this disclosure.

FIGS. 9A-9C illustrate examples of a joint line on a model of patient anatomy displayed on a user interface, in accordance with at least one example of this disclosure.

DETAILED DESCRIPTION

Figure 1:
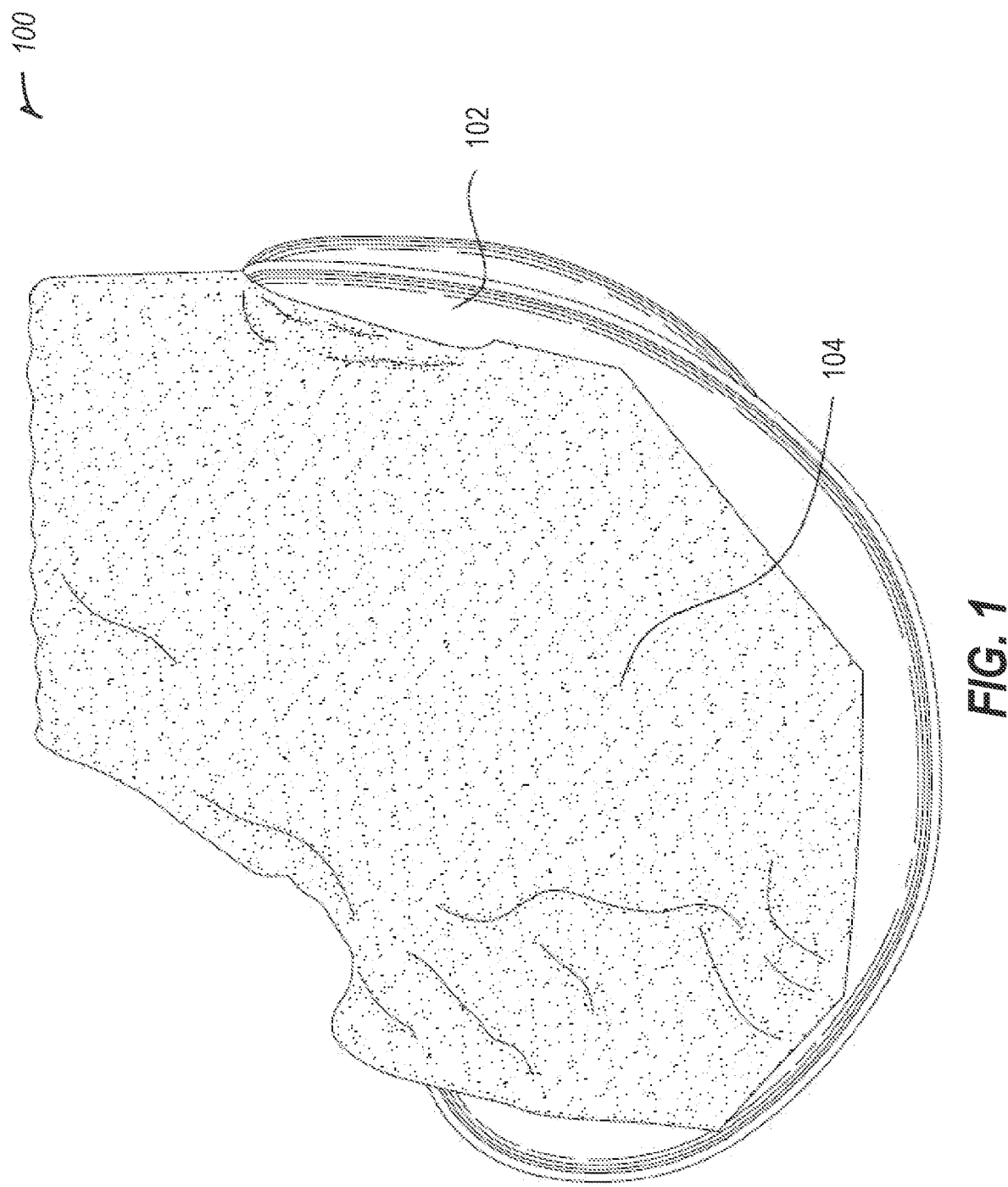
FIG. 1 illustrates a model of a knee, including an implant, of a patient undergoing a revision procedure on the knee in accordance with at least one example of this disclosure.

Systems and methods for performing a revision using a tensor device are described herein. These systems and methods herein may be used for performing a revision knee arthroplasty. In an example, a robotic surgical device may be used with the tensor device.

Revision surgery includes removing a previous implant and placing a new implant. The systems and methods described herein use a tensor device, and optionally a robotic surgical device to assist in portions of the revision surgical process. For example, a robotic surgical device may be used for measurements, as a cut guide, to autonomously make cuts, as a force assist device, or the like.

Use of the tensor device may improve precision, for example for joint alignment or to adhere more closely to a plan or replan. The tensor device may be used in a knee revision procedure. A knee revision procedure includes balancing the knee, which may include a varying degree of difficulty and satisfaction for a patient. The tensor device described herein may connect to ends of reamer shafts in canals of a femur and a tibia of a patient, and provide accurate and quick gap balancing information, joint line information, or implant information.

The tensor device described herein may be connected to an end portion of a reamer for a femur and an end portion of a reamer for a tibia. A lock (e.g., a crank) may be rotated, for example with a screwdriver, to identify an extension gap or a flexion gap. A portion of the tensor device may visually indicate a gap, or a user interface on a display screen may display a gap, for example using a robotic surgical device to provide location or tracking information. The robotic surgical device may be used to control or maintain a position of a portion of the tensor device, or may be used independently of the tensor device (e.g., for location information using the robotic surgical device's coordinate system within a surgical field).

The tensor device may be used to set a desired tension of the knee joint in flexion or extension. The tension may be locked to set the desired tension. Locking may be performed using a screwdriver or other tool, for example. The tensor device may include any one or combination of an indicator of a joint line, an indicator of an implant size, an indicator of a gap size, or the like. The indicator may be changed with a slideable portion of the tensor device. The slideable portion may move based on a change between relative positions of reamer ends of stems in a femur and tibia. For example, the tensor device may include a portion affixed to an end of a reamer in the femur and a portion affixed to an end of a reamer in the tibia. The tensor device may be used with a joint line process to determine one or more of an implant size, a cut, a spacer size, or the like.

The tensor device may be used as a cutting block or to provide a location for a cutting block. For example, once positioned into place, the tensor device may provide one or more cutting slots for an anterior cut, a posterior cut, or the like.

The tensor device may be used to determine an offset from a reamer (e.g., the tibial reamer or femoral reamer). The offset may be determined using the robotic surgical device, which includes an internal coordinate system for tracking locations of various aspects of knee anatomy and the tensor device. The tensor device may be used to provide information related to an augment determination, for example using the robotic surgical device.

A tensor device may include a femoral component couplable with an end portion of a femoral intramedullary canal reamer (e.g., a handle portion, or a portion extending out from the femur, such as when the reamer is in the femur) and a tibial component couplable with an end portion of a tibial intramedullary canal reamer. The femoral component and the tibial component may be directly connected, slideably connected, or connected via another component, such as a slider component. A slider component may be slidably affixed to the femoral component and the tibial component. In an example, the slider component is configured to slideably adjust a distance between a portion of the femoral component and a portion of the tibial component, such as to identify a knee gap, an implant size, and/or a joint line. The knee gap may be identified in extension or flexion. The tensor device may include a lock, for example to set a configuration or position of the tensor device in place relative to the tibia and/or femur.

The robotic surgical device may be used with the tensor device. For example, the robotic surgical device may be used to identify one or more of an end of a stem, a location of a portion of the tensor device, or information related to the knee. For example, the robotic surgical device may be used to determine an offset of a stem based on tension in the tensor device, such as using a known position within a coordinate system of the robotic surgical device.

In some examples, the tensor device may be used to replace a trial. For example, the tensor device may be used (with or without the robotic surgical device) to determine an offset without the use of a separate offset determination adapter. The trial may be used in an example to verify or check the offset determined using the tensor device.

FIG. 1 illustrates a model 100, including an implant 102 affixed to a bone 104 of a knee of a patient undergoing a revision procedure on the knee, in accordance with at least one example of this disclosure. The model 100 may be generated using imaging techniques, such as from two x-rays, for example a frontal and a lateral x-ray. These two x-rays may be lined up and a model may be generated using a 3D projection or estimation of the patient anatomy. Other imaging techniques may be used, such as, MRI scanning, CT scanning (computerized tomography), fluoroscopy, or like radiography methods, for example any that provide suitable resolution of images.

In an example, the patient anatomy may be modeled preoperatively, and used to plan steps of a revision surgical procedure. Deviations from the plan may occur during the procedure, and modifications to the plan (e.g., replanning) may occur intraoperatively, particularly when using a robotic surgical device.

In an example, the model 100 may be generated intraoperatively, for example using registration and optical navigation. The model 100 may not be a fully rendered 2D or 3D model of the patient anatomy, but may instead include key points, interpolated or extrapolated points, or other information used for completing a revision procedure. The points may be captured intraoperatively, for example using a digitized technique.

Digitizing points on the knee may be achieved with discrete registration of points or may be achieved by painting portions of the knee. The intraoperative registration of the model 100 may be performed preoperatively and intraoperatively, in an example. The registration may be performed after the revision is completed or a portion of the revision is completed, such that a surgeon may evaluate the post-revision knee or use the intraoperative image and preoperative images to compare the knee before and after the revision. An example method for generating the model 100 may be found in U.S. Pat. No. 7,715,602, titled "Method and apparatus for reconstructing bone surfaces during surgery," which is hereby incorporated by reference herein in its entirety.

In an example, when the model 100 is generated preoperatively, the model 100 may be used to plan the revision. When the model 100 is generated intraoperatively, the model 100 may be used to modify a preoperative revision plan. In either example, a joint line for the knee of the patient may be used or generated. Generation or use of the joint line, as well as planning with the joint line are described further below, with respect to FIGS. 2, 7, and 8.

The models described with respect to the patient anatomy need not be actually rendered or displayed. Instead, the models may be used by a robotic surgical device to perform portions of a revision procedure. For example, coordinates of registered points and interpolated or extrapolated other points, simulation of coordinates as moved or cut during a procedure, or the like may be stored in memory. A robotic surgical device may retrieve data stored in the memory when performing a portion of the revision procedure.

The model 100 may be used as a model for planning cuts during an implant removal step of a patent application for robotic knee revision. In an example, the diagram 100 may show a live version of patient anatomy, a modeled version, or the like.

The model 100 may be based on captured images (e.g., an x-ray, CT, MR, etc.). The model 100 may indicate various aspects of the patient anatomy and other aspects of the surgical field. For example, based on modeling (e.g., using machine learning, binary classification, or the like), the bone 104 or a portion of the bone 104 may be highlighted in the model in a first manner (e.g., a color, a transparency, etc.). In an example, cement attached to the bone 104 or the implant 102 may be highlighted in the model 100 in a second manner. The pre-operative imaging may indicate what is bone and what is cement, for example based on color, density, etc., in the medical image. The implant 102 may be highlighted in a third manner, in an example. A pre-operative plan created using the model 100 may include consideration of the areas that are cement, to guide a surgeon to remove the cement. Cement is radio-opaque, so it may be identified using an x-ray.

Other details of the patient anatomy or instruments may be highlighted or identified in the model 100. For example, details about the implant 102 may be identified. These details may include a size of the implant 102, a type of the implant 102, a manufacturer of the implant 102, a placement or location of the implant 102 relative to patient anatomy, or the like. An image of the implant 102, captured via an x-ray or other medical imaging, for example, may be compared to stored images of implants to determine a size, type, or manufacturer of the implant 102. In another example, a size of the implant 102 may be determined based on a known size of the bone 104. The determined size of the implant 102 may include an estimate. The size may include an anterior-posterior size, an anterior-posterior box dimension, or medial-lateral width, in an example. In some examples, the manufacturer of the implant 102 may be identified based on identifying marks or words on the implant (e.g., an engraving), via a particular style or shape, or the like.

In an example, the model 100 may be used in a robotically assisted revision surgery to remove a worn-out implant (e.g., implant 102). In this example the model 100 may be used to plan the robotically assisted revision surgery. In some examples, a tensor device, as described herein may be used in the robotically assisted revision surgery.

Figure 2:
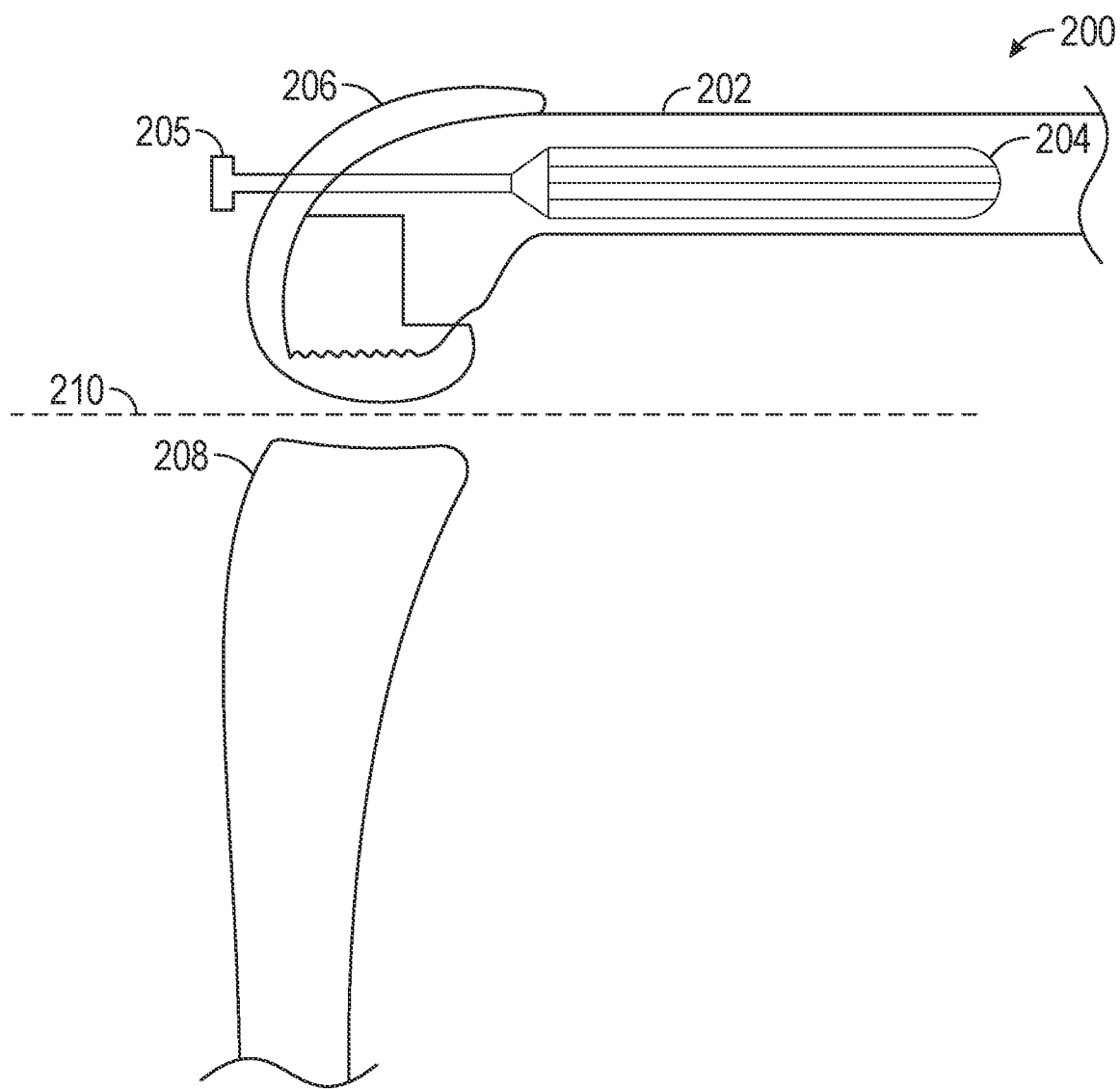
FIG. 2 illustrates a femoral reamer acting as a reference within a femur in accordance with at least one example of this disclosure.

FIG. 2 illustrates a user interface 200 showing a surgical field including a femoral reamer acting as a reference in accordance with at least one example of this disclosure. The surgical field includes a femur 202, a reamer 204, a reference attachment portion 205 of the reamer 204, and a tibia 208. The user interface 200 includes a joint line 210 (e.g., a joint line that is preplanned, intraoperatively identified, estimated, one of two or more potential joint lines, etc.) and a model of an implant 206.

In an example, the joint line 210 is preplanned (e.g., preoperatively). The implant model 206 may be generated using the joint line 210 and the reference attachment portion 205 of the reamer 204. The joint line 210 may be moved by a surgeon on the user interface 200, resulting in a new or updated implant model 206 being displayed.

In an example, the user interface 200 includes an overlay of an intraoperatively determined femur model implant 206 size. The model implant 206 may be positioned posteriorly to determine whether the model implant 206 matches the femur 202 and an identified size for an implant (e.g., identified using a tensor device or a surgical robotic device) on the user interface 200. As further illustrated and discussed in reference to FIGS. 4A-4D, the identified size of the implant may be determined by a tensor device, for example by connecting the tensor device to a reference attachment portion of an actual reamer device inserted in the femur of the patient corresponding to the reference attachment portion 205 displayed on the user interface 200. In this example, the tensor device may include an indication of an implant size for the femur 202. For example, on the tensor device, a selectable marker may be adjustable according to a joint line (e.g., corresponding to the joint line 210 displayed on the user interface 200). The surgeon may select a joint line on the tensor device, and the implant size may be determined or shown on the tensor device.

In an example, a robotic surgical device may be used to determine the implant size, for example by identifying locations of the tensor device. The robotic surgical device may output (e.g., via a controller, sensors, or the like) information related to an implant size, and an identified implant size may be displayed on the user interface 200. The display may include a size value or an overlay of the identified implant. In an example, two model implants may be displayed and adjusted until aligned. For example, a first model implant 206 may be identified using the joint line 210 and a second model implant may be identified from the tensor device, the robotic surgical device, or a combination of the two. A surgical robotic device may be used to output a maximum medial or lateral size of a femoral implant. A femoral implant size may be chosen and optionally displayed based on the maximum size.

Further details about the implant model 206 may be determined using the user interface 200, the tensor device, or the robotic surgical device, such as a stem offset for the reamer 204. The stem offset may be a few millimeters, such as three or six.

Figure 3:
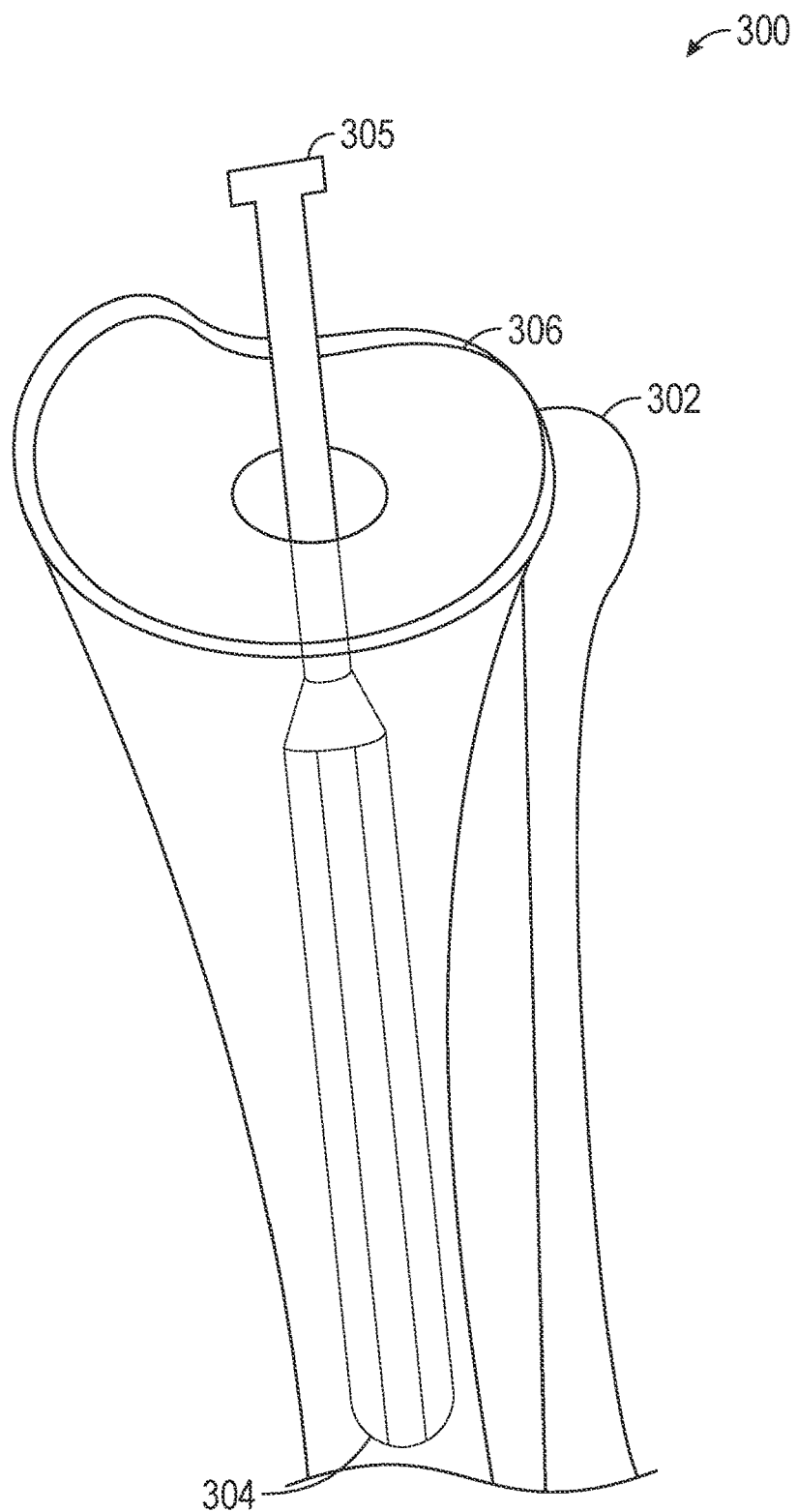
FIG. 3 illustrates a tibial reamer acting as a reference within a tibia in accordance with at least one example of this disclosure.

FIG. 3 illustrates a user interface 300 for determining or estimating a tibial offset, for example using a tibial reamer reference in accordance with at least one example of this disclosure. A surgical field shown within the user interface 300 includes a tibia 302, a reamer 304, and a reference attachment portion 305 of the reamer 304. The user interface 300 includes a model of a tibial offset 306.

In an example, the user interface 300 may be used to provide the tibial offset model 306 according to a determined size. The size may be determined using a preoperative plan, a tensor device, a robotic surgical device, or a combination of two or more of these. In an example, a tibial implant may be positioned on the user interface 300, for example by a surgeon. Using the positioned location, a robotic surgical device may correlate the location to a reamer end portion (e.g., corresponding to the reference attachment portion 305 of the reamer 304 represented in the user interface 300) to determine an offset.

FIGS. 4A-4D illustrate a tensor device in various views in accordance with at least one example of this disclosure.

Figure 4A:
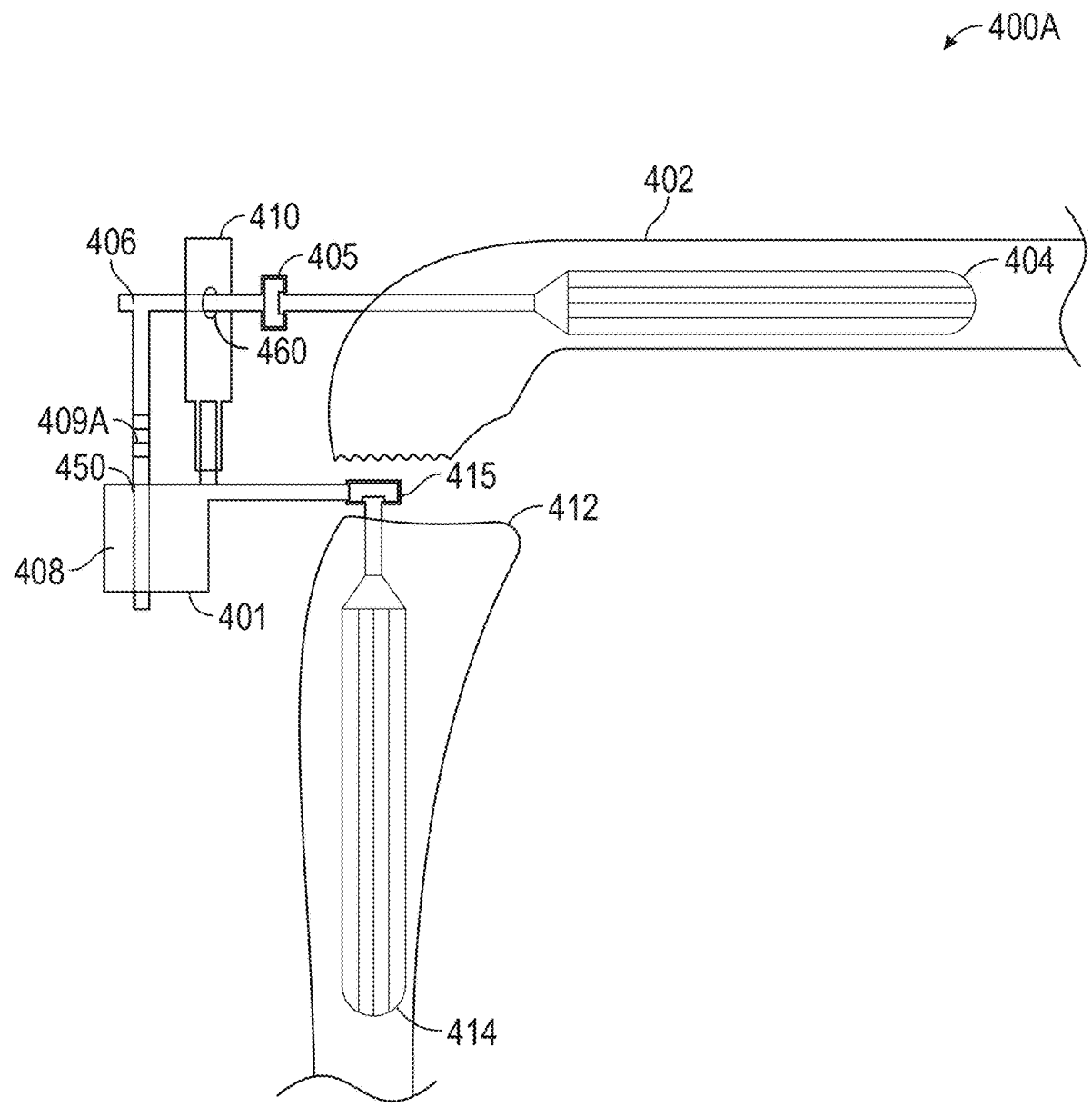
FIGS. 4A-4D illustrate a tensor device in various views in accordance with at least one example of this disclosure.

FIG. 4A illustrates a first view 400A with a knee in flexion, the first view 400A including a first configuration of the tensor device 401. In the first view 400A, various components of the tensor device 401 are shown, including a femoral arm 406 configured to couple with an end portion 405 of a femoral intramedullary canal reamer 404, which is shown in a femur 402. The tensor device 401 includes a tibial arm 408, which may be moveably connected to the femoral arm 406. The tibial arm 408 may be configured to couple with an end portion 415 of a tibial intramedullary canal reamer 414, which is shown in a tibia 412. The tensor device 401 is shown in the first view 400A as including a slider component 410, which may be coupled (e.g., encircling, attached, or affixed) to the femoral arm 406. The slider component 410 may be coupled to the tibial arm 408. The slider component 410 may slide based on movement of the femoral arm 406 or the tibial arm 408. The slider component 410 may include one or more visual indicators (e.g., indicator 409A) that are configured to change as the slider component 410 slides. The one or more indicators may identify a joint line, a knee gap, an implant size, or the like.

In an example, the slider component 410 may be used to identify an offset for the femoral intramedullary canal reamer 404 from a central axis of the femur 402 or the joint line. An offset from a central location of the femoral arm 406 within an opening of the slider component 410 may be used to determine the offset for the reamer 404.

Figure 4B:
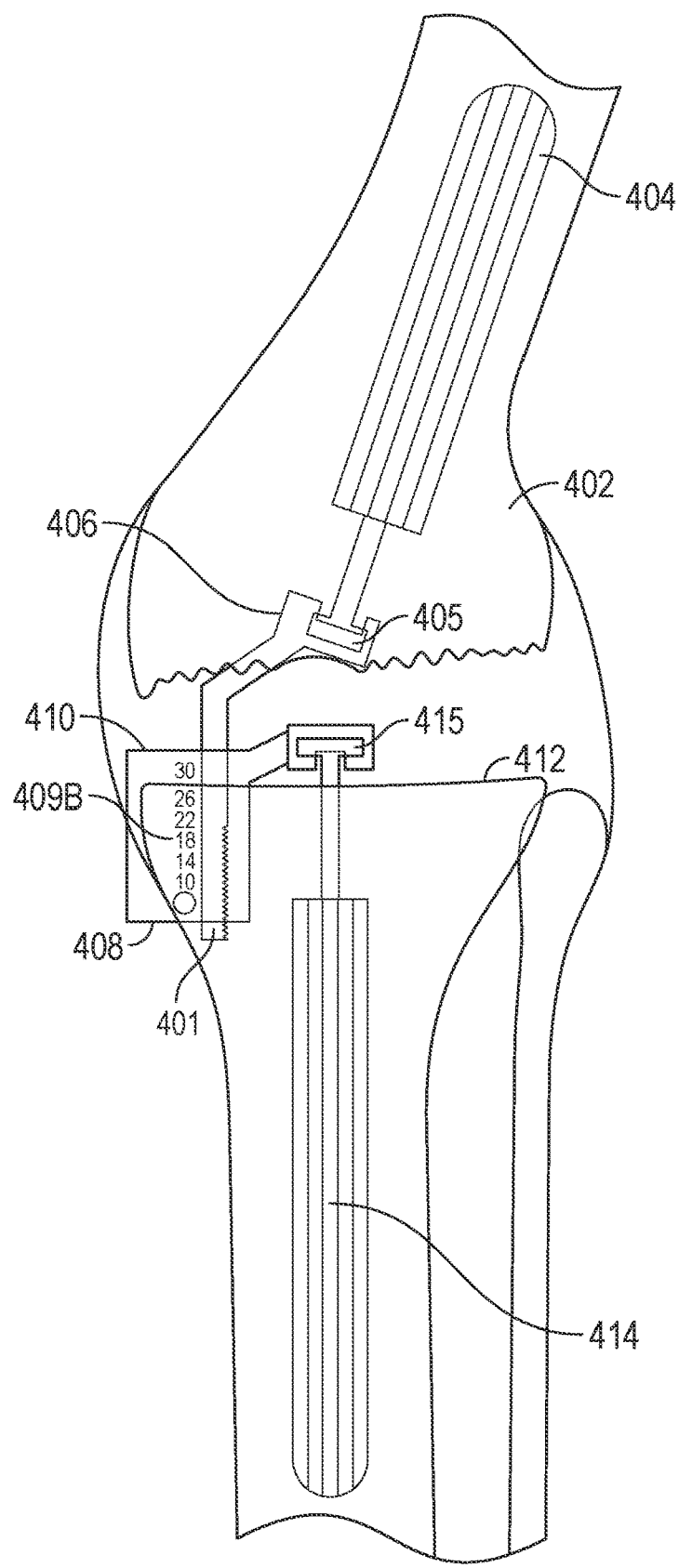

FIG. 4B illustrates a second view 400B with the knee joint modified from the configuration of the first view 400A to be in extension. The second view 400B includes a second configuration of the tensor device 401. The second view 400B illustrates the femur 402 and the tibia 412 in extension. In this position, the tensor device may be used to assess ligament balance in the knee. The slider component 410 may include one or more a visual indicators to output a joint line, a femoral component size, or the like. The second view 400B illustrates another example indicator 409B.

Figure 4C:
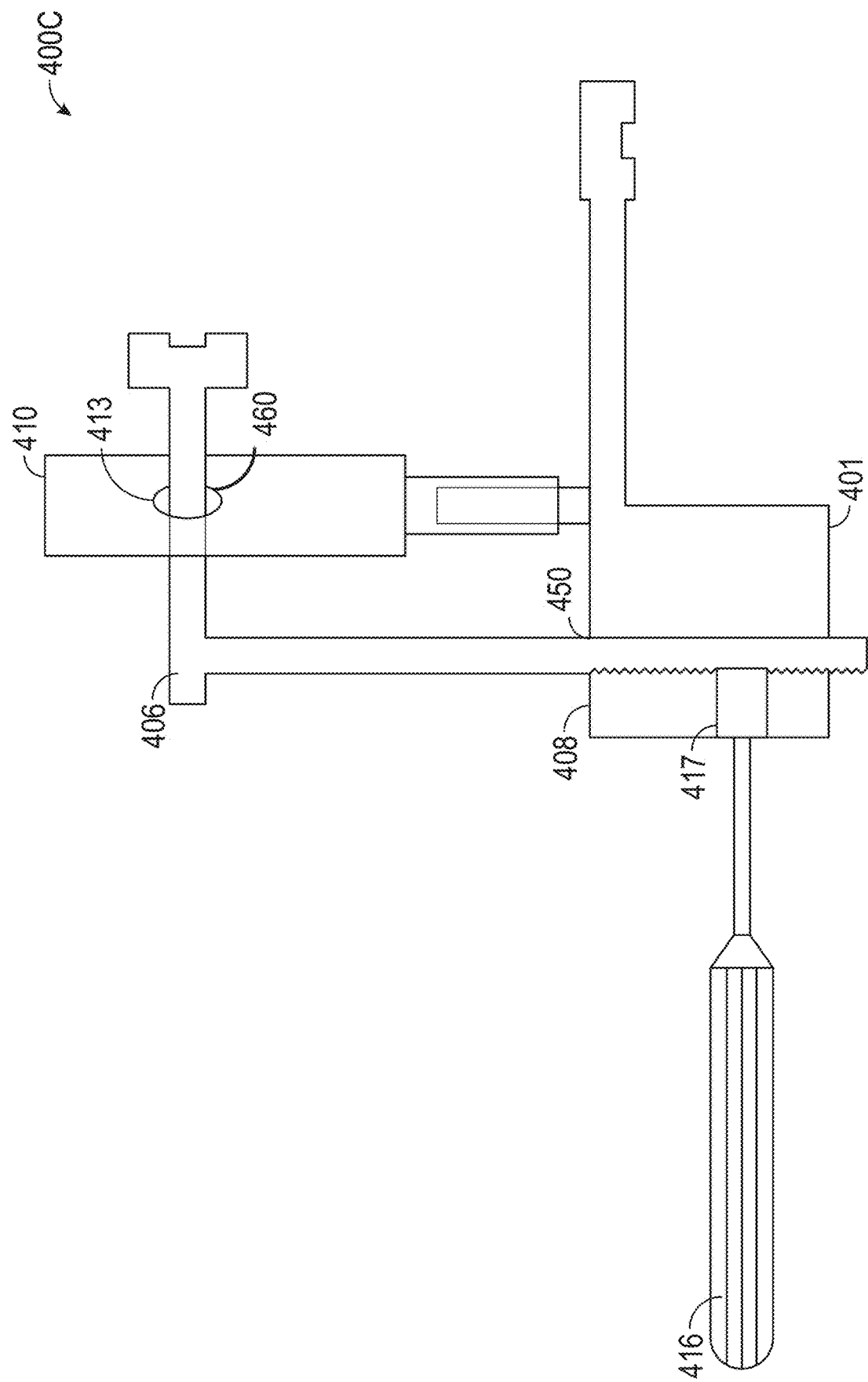

FIG. 4C illustrates a side view 400C of the tensor device 401 with the knee in a flexion position. The side view 400C illustrates a screwdriver 416, which may be used to tighten or crank the femoral arm 406 portion of the tensor device 401 relative to the tibial arm 408, such as to move or lock the tensor device 401 in a particular configuration. The screwdriver 416 or another device or a surgeon's hand may be used to operate a lock lever 417 to lock the tensor device 401 (e.g. with respect to a configuration). The slider component 410 may include an aperture 413 through which the femoral arm 406 may move. As shown in FIGS. 4A and 4C, the femoral arm 406 being movably connected to the tibial arm 408 forms a first connection 450 between the femoral arm 406 and the tibial arm 408. The tibial arm 408 and the slider 410 forms a second connection 460 between the femoral arm 406 and the tibial arm 408.

Figure 4D:
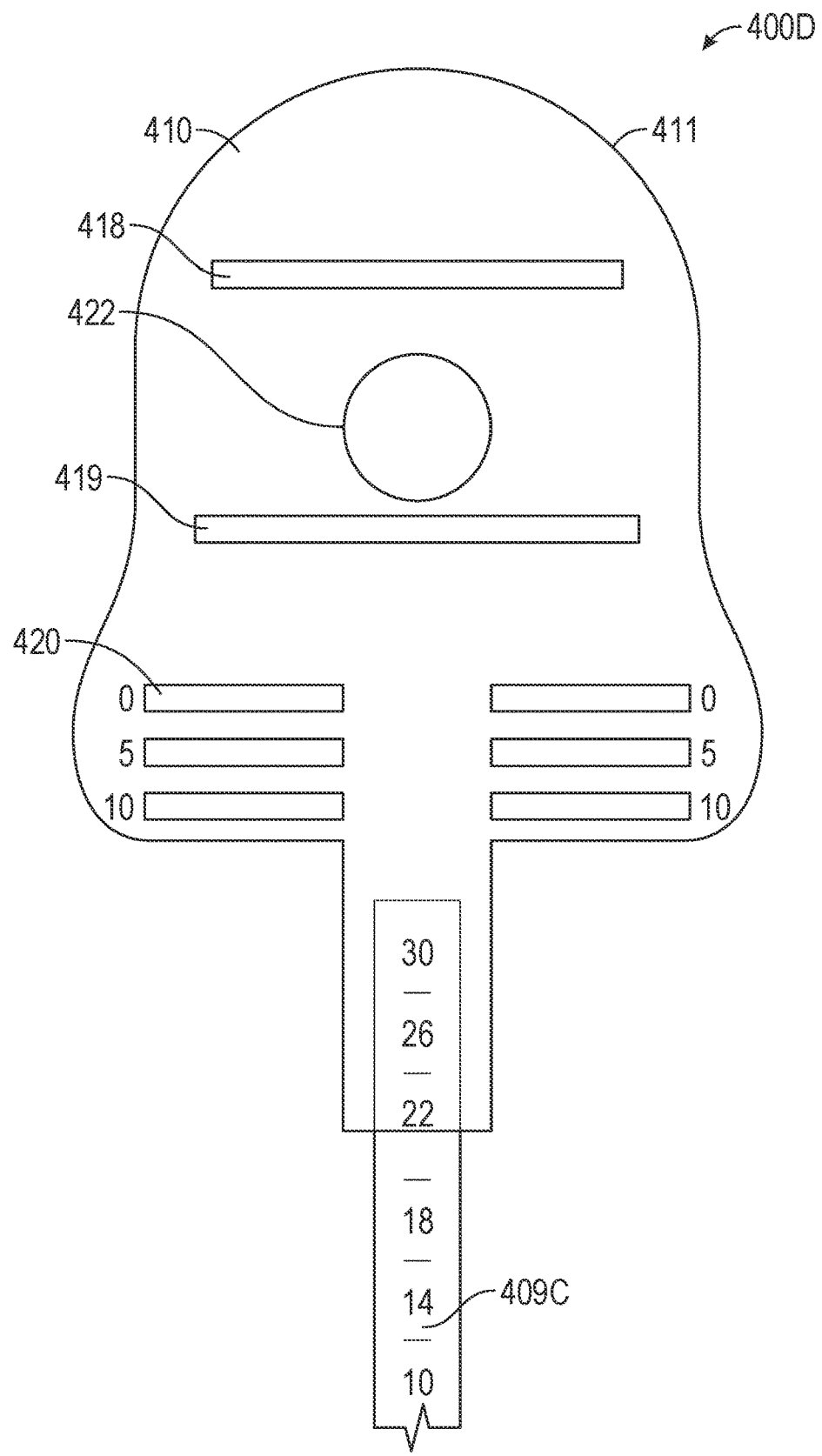

FIG. 4D illustrates a front view 400D of the tensor device 401 with the knee in a flexion position. The front view 400D illustrates an example configuration of the tensor device 401 that includes an optional cut guide 411 as part of the slider component 410 or as a separately mountable component in addition to or used in combination with the slider component 410. The cut guide may include one or more slots to be used as a cut guide. For example, a top slot 418 may be used for an anterior cut, a bottom slot 419 for a cut, and lower slots (e.g., slot 420) for posterior cuts, which may be selected depending on augment needed. In an example, the tensor device 401 may be used to determine a size of an augment needed, as described herein. An offset dial 422 may be used to determine an offset needed for a reamer. In an example, the offset dial 422 may not be tight around the femoral arm 406, instead the offset dial 422 may be configured to allow it to move around the femoral arm 406, which may be used to identify an offset for a femoral reamer. The front view 400B illustrates another example indicator 409C. The offset dial 422 may be an indicator or component of an outer portion of the aperture 413 of FIG. 4C.

When the knee of a patient is in flexion, the tensor device 401 may serve as a femoral cutting block with augment resection slots and for femoral stem offset determination. A bottom portion of has a lock lever 417 to lock the tensor device 401, when affixed to the knee in flexion, in a configuration that matches an extension gap. In an example, if the tensor device does not allow positioning to close the flexion gap enough to match the extension gap, then an indicator on the slider may account for up to 3 mm more closure of the posterior gap, for example with a plus sized femur. In an example a surgeon may select a joint line (e.g., via an indicator on the tensor device 401) and the tensor device 401 may be adjusted to determine a femoral component size.

FIG. 5 illustrates a flowchart illustrating a technique 500 for using a tensor device in accordance with some embodiments. In an example, operations of the technique 500 may be performed by processing circuitry, for example by executing instructions stored in memory. The processing circuitry may include a processor, a system on a chip, or other circuitry (e.g., wiring). For example, technique 500 may be performed by processing circuitry of a robotic surgical device (e.g., using a control system).

The technique 500 includes an operation 502 to receive an indication including a joint line of a knee for a revision procedure. The technique 500 includes an operation 504 to cause a robotic arm to align a femoral arm of a tensor device parallel to an intramedullary axis of a tibia while a tibial arm of the tensor device is connected to an end portion of a tibial reamer.

The technique 500 includes an operation 506 to determine a component size for an implant or a knee gap based on the alignment of the femoral arm. In an example, the implant is a femoral implant or a tibial implant. The component size may correspond to a knee gap, for example based on an alignment of a portion of the tensor device, such as the femoral arm, a slider component, a gap indicator, or the like. The knee gap may be identified based on an angle, tension, offset of femoral component, or indicator in flexion or extension.

The technique 500 includes an operation 508 to output the component size or the knee gap for display in a user interface. The user interface may include part of a planning application, and wherein the indication is received on the user interface, such as via a surgeon selection.

The technique 500 may include an operation to receive an adjustment to the joint line (e.g., using the user interface), and an updated component size may be output. An example output (e.g., for display on the user interface) may include a recommended femoral or tibial cut, range of motion information (e.g., tension at various points along a range of motion, such as from zero degrees in extension to 90 degrees in flexion), varus or valgus values throughout a range of motion based on tension values identified throughout the range of motion, a 3D model of the patient knee (e.g., based on a plurality of digitized points on the knee), or the like.

The technique 500 may include controlling the robotic arm to position the arms of the tensor device to assess ligament balance in extension or determine whether ligaments are valid in flexion. The technique 500 may include determining a femoral component offset using robotically determined canal and posterior condyles locations, a location of a tibial cut surface, or a ligament tension at extension. In an example, an augment or information about placement, size, or type of augment, may be determined based on known locations (e.g., identified via the robotic arm) or the joint line.

FIG. 6 illustrates a robotic surgical system 600 including a robotic surgical device 602 (e.g., a robot or a robotic arm) and a computing device 604 (e.g., a device having a processor) in accordance with at least one example of this disclosure. In an example, the robotic surgical device 602 and the computing device 604 may be coupled, such as communicatively coupled or physically connected.

The system 600 optionally includes an optical navigation system 606, which may detect a location of an optical navigation device 610. The system 600 is shown in relation to a patient 608. The patient 608 may be undergoing a revision procedure, for example to remove an existing implant and optionally receive a new implant. The robotic surgical device 602 may be used to perform aspects of the revision procedure.

The system 600 is illustrated with a tensor device 612 affixed to an end effector of a robotic arm of the robotic surgical device 602. The tensor device 612 may be placed using the robotic surgical device 602. In an example, the tensor device 612 may be manually affixed to femoral or tibial reamers while affixed to the end effector. The robotic surgical device 602 may be used to manipulate or lock the tensor device 612 in place (e.g., at a selected joint line, gap, etc.). The robotic surgical device 602 may be used to determine a joint line, gap, or the like based on a location of the tensor device 612 (e.g., using the optical navigation system 606).

In an example, a bone or bones of the patient 608 may be modeled before an existing implant is removed. The current bone and implant model may be in a virtual 3D format. For example, frontal and lateral images of the bone and implant may be used to generate a current bone and implant model (e.g., via a front and a lateral x-ray). In another example, a 3D bone model may have been previously generated during implantation of the existing implant. The 3D bone model may be obtained and updated from the existing implant procedure.

In an example, a model of the bone comprises a surface geometry of parts of the bone that are exposed despite the presence of the implant or the limitations of the imaging. The model of the bone may include a surface geometry of the implant relative to adjacent bone surfaces, and a 3D geometry of the implant, for example using a 3D model of the implant (e.g., from the manufacturer, etc.).

The bone modeling may include generating a 3D surface of the bone when the bone modeling is not directly performed by the imaging equipment, or if not complete. In an example in which multiple implants are to be replaced (e.g., a total knee revision), all bones supporting implants may be modeled. Additional structures may be modeled as well, such as cartilage, hip joint, hip, ankle, etc.

In terms of planning, an operator may select a position or orientation of a 3D model of a replacement implant (e.g., a new implant) that is to be used in a revision surgery. In another example, the position or orientation may be automatically generated (e.g., using machine learning). Further planning may include determining a location for a cut plane to support the replacement implant. The planning may be assisted by an overlay of the revision implants on the bone models.

In an example, an intramedullary rod may be implanted to reinforce a bone. The planning may include determining a placement of an intramedullary rod (e.g., an orientation or position) using the robotic surgical device 602. For example, the robotic surgical device 602 may identify or may use a mechanical axis to place the rod or hollow out a canal for placement of the rod. In an example, the medullary cavity may be hollowed out by the robotic surgical device 602. Additional information including location or orientation of an intramedullary canal or an epicondylar axis may be used.

The 3D model of the bone with implant may comprise data pertaining to the surface geometry of a relevant portion of a bone and of the implant, including surfaces of the bone that are exposed despite the presence of the implant. The 3D model of the bone with implant may also include joint line information, full bone models with implants, mechanical axes, center of rotations, etc. The 3D models may also include a bone and revision implant planning model with an identification of implants that may be used, and bone alteration models to receive the implants and other accessories (intramedullary rods) based on surgical planning.

In an example, the robotic surgical device 602 may be used to cut the bone, for example using a reference guide incorporated in a tensor device. The robotic surgical device may autonomously perform the cut (e.g., using the optical navigation system 606 to guide the robotic surgical device 602). In another example, the reference guide incorporated in the tensor device may be used without the robotic surgical device 602.

The optical navigation system 606 may track the optical navigation device 610, which may be affixed to a bone or an implant of the patient, or affixed to a portion of the robotic surgical device 602. Several optical navigation devices (e.g., trackers) may be used, for example one on each of a femur, tibia, the robotic surgical device 602, and an existing implant. From the tracking information gathered by the optical navigation system 606, used to track each of the optical navigation devices, the robotic surgical device 602 may be guided to perform a cut (e.g., to remove the existing implant).

After the existing implant has been removed (by the surgeon or by the robotic surgical device 602 autonomously or collaboratively as a force assist or force prevention device), the robotic surgical device 602 may be used to reregister a surface of the bone or replan a new implant (e.g., modify a preoperative plan intraoperatively).

In an example, the computing device 604 may predict what anatomy of the patient's bone looked like (e.g., before the existing implant degraded, before the existing implant was put in, or before the existing implant was needed, such as when the bone was healthy). From the predicted anatomy, a model may be generated or kinematic information may be determined.

An example technique using the robotic surgical device 602 may include performing a cut to remove an existing implant (e.g., using the robotic surgical device 602). The technique may include mapping an existing surface (e.g., an articular surface), and predicting the surface in a prior state. A tensor device may be used as a cut guide to perform a cut on the existing surface based on kinematic information of the predicted surface.

The robotic surgical robot 602 may be used to determine a level of constraint. For example, with a particular amount of laxity detected by the robotic surgical robot 602, a corresponding level of constraint may be used. The level of constraint may be determined based on how much constraint the component system provides due to the loss of ligament or patient anatomy (e.g., hinges are a high level of constraint, posterior stabilized may be a lower level of constraint).

The robotic surgical device 602 may be used to provide stability during a procedure. For example, the robotic surgical device 602 may maintain control of a level of constraint (e.g., a particular amount of laxity may correspond to a particular level of constraint). The level of constraint may include how much constraint a component system provides due to the loss of ligament or patient anatomy (e.g., hinges are a high level of constraint).

The level of constraint may be selected by a surgeon, with suggestions displayed on a user interface. The suggested level of constraint may be displayed during a surgical procedure. For example, a next higher level of constraint may be suggested when detected laxity has reached or exceeds a particular level. In an example, when a basic poly or ultra-congruent is used, the robotic surgical device 602 may determine that laxity has reached a particular level and a user interface may display a suggested next-level of constraint. The correspondence of laxity level to constraint level may be based on a model or a set of features, used to determine when a next level of constraint is needed. The robotic surgical system 600 may output a warning alert, for example an audible or visible alert via the robotic surgical device 602 or a user interface of the computing system 604. In an example, the level of constraint may be determined using an indicator of a tensor device, as described herein.

The robotic surgical device 602 may be used to determine locations of various aspects of the surgical field. For example, the locations may be determined within a coordinate system of the robotic surgical device 602. For example, the robotic surgical device 602 may determine a location of an end of a reamer and adjust a configuration of a tensor device. In an example, once configured, the tensor device may indicate a joint line, a component size, or the like. In another example, once configured, the robotic surgical device 602 may output an indication of a joint line, a component size, or the like, for example by outputting information for display on a user interface.

In an example, canals may be reamed for stems, for example with stems sturdy enough to use the tensor device. The tensor device and the robotic surgical device 602 may be used to output an offset for a stem. The location of the stem with respect to the bone may be identified using imaging, such as based on an optical camera, or via digitized information of the femur or tibia.

In an example, the robotic surgical device 602 may be used to perform a range of motion test on the knee. The range of motion may determine varus or valgus angles throughout the range of motion, for example at each of a few angles, such as 0 30 60 90 flexion, etc.

Figure 7:
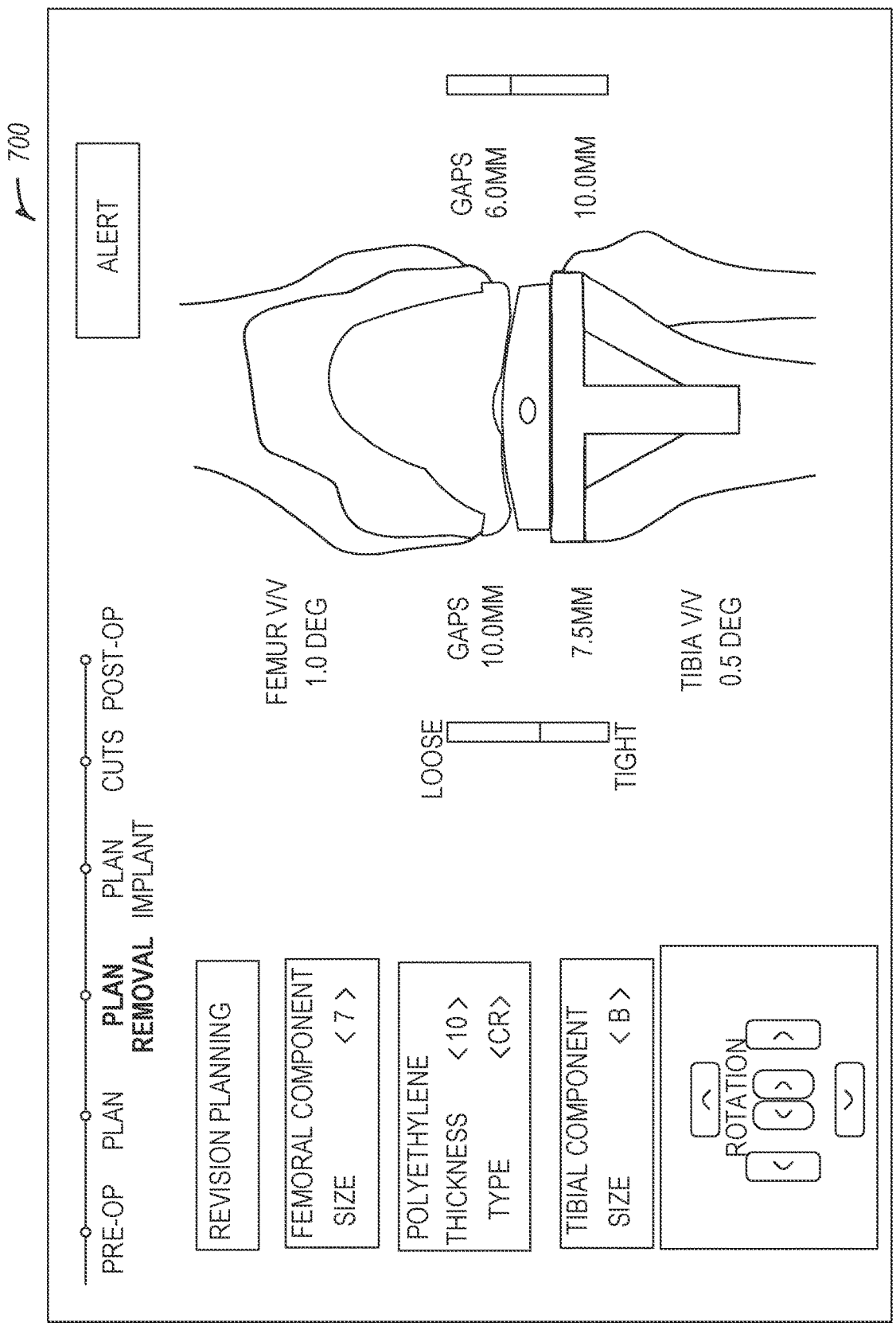
FIG. 7 illustrates a user interface for planning aspects of a revision (e.g., a cut, a new implant, a joint alignment, etc.) in accordance with at least one example of this disclosure.

FIG. 7 illustrates a user interface 700 for planning aspects of a revision (e.g., a joint alignment, a cut, placement of a new implant, etc.) in accordance with at least one example of this disclosure. For example, the user interface 700 may be used for removal planning, new implant planning, control of a robotic surgical device, control of system components, or the like.

During pre-operative planning, existing hardware (e.g., an implant) may be identified and displayed on the user interface 700. The user interface 700 may be used to preoperatively plan aspects of a revision process. For example, a joint line may be selected, a new implant size may be determined, a cut may be planned, an offset may be determined, or the like.

Figure 8:
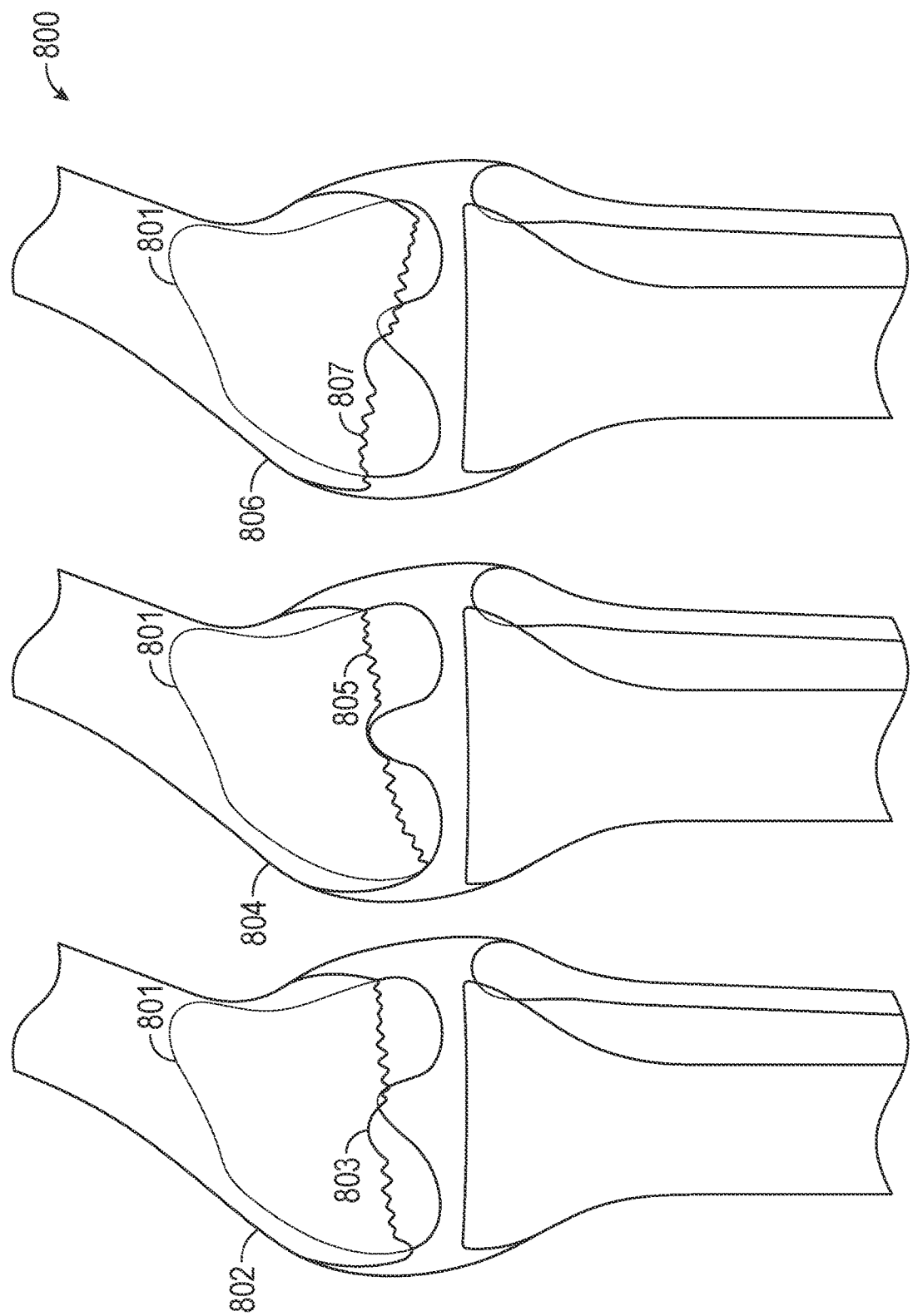
FIG. 8 illustrates a user interface for flexion gap balancing in accordance with at least one example of this disclosure.

FIG. 8 illustrates example models for flexion gap balancing in accordance with at least one example of this disclosure. One or more of the example models may be displayed in a portion of the user interface 700. The example models may be used for flexion gap balancing preoperatively or intraoperatively.

The example models include different femurs 802, 804, and 806, with current bone lines 803, 805, and 807. In each of the three example models, a model of missing bone 801 may be located at the same location in each example. The model of missing bone 801 may be generated based on a parallel line offset from the tibia. The parallel line for placement of the model of missing bone 801 may be based on a planned joint line. A location for a reamer may be generated based on the model of missing bone 801.

A tensor device, as described herein may be used to balance the knee based on the joint line, the model of missing bone 801, and the location for the reamer. For example, once the reamer location is identified, the reamer may be placed in the femur and a reamer may be placed in the tibia, and the tensor device may connect to the two reamers, to identify a knee gap. In an example, the tensor device may optionally not be hooked to the reamer, such as when the bone is off good quality and surgeon is not using an offset.

Figure 9C:
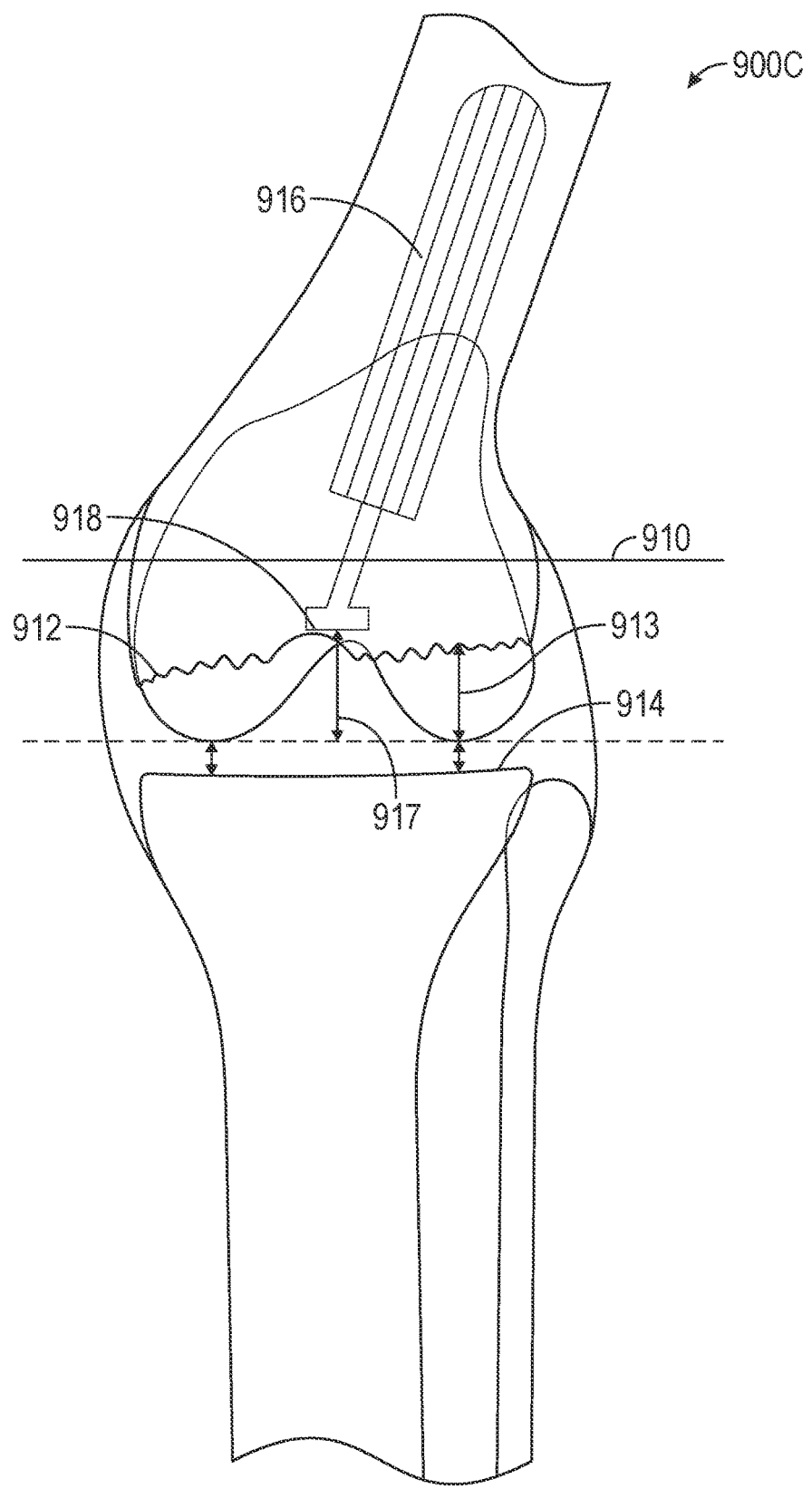

FIGS. 9A-9C illustrate example views 900A, 900B, and 900C of a joint line on a model of patient anatomy in accordance with at least one example of this disclosure. A plurality of joint lines 902, 904, and 906 are shown in example 900A, while a single joint line 908 is shown in examples 900B and 900C. In some examples, example 900A is a first view, and one of examples 900B or 900C is a second view of the same patient anatomy.

A joint line is a reference line relative to aspects of knee anatomy of a patient (e.g., a mechanical axis, a kinematic axis, an axial line of a bone, such as the femur or tibia, landmarks of the femur or tibia, etc.). The joint lines (e.g., 902, 904, 906, 908, or 910) displayed may indicate estimations of the joint line to be used for a revision procedure on a knee represented in the example views 900A, 900B, or 900C.

In an example, a robotic surgical device may be used as well during a revision. For example, the robotic surgical device may provide stability to a bone or implant during a portion of the procedure. In an example, the robotic surgical device may collect data (e.g., sensor data). In an example, the robotic surgical device may be used with optical navigation to perform a burr during the techniques described herein. The robotic surgical device may be used to hold a cut guide for performing a cut (e.g., to remove bone or an existing implant). In some examples, a robotic surgical device may be used to register aspects of a bone or implant, such as with the existing implant in (e.g., intraoperatively) or after the existing implant is removed. The robotic surgical device may be used to provide assistance with cuts. The robotic surgical device may provide a reference to a joint line (e.g., having a degree of varus or valgus), provide a recreation of a joint line (e.g. using modeling techniques), provide predictive analytics of a projected joint line (e.g., based on previous implant, new implant, or probability prediction), or the like. Recreation of joint line or other bone recreation may include identification of joint line parameters by using a digital implant 3D model as overlaid onto the image of bone and implant.

The robotic surgical device may collect data, such as the joint line information described above or a thickness of revision. The robotic surgical device may allow for intraoperative adjustments, replanning, or additional precision (e.g., to leave more bone in the patient and less cut off than in traditional techniques).

In an example, a single joint line may be displayed (e.g., a joint line with a highest probability estimated using robotic measurements of landmarks), or multiple joint lines (e.g., with small variations) may be displayed for a surgeon's selection. The joint line or lines may be determined by extrapolating from available landmarks or using robotic sensing. Typical landmarks to identify a joint line preoperatively may not exist or may not be identifiable in a revision procedure (e.g., due to previously cuts, obscured by an existing implant, bone deterioration, or the like). In an example, an epicondyle landmark may be used in a revision procedure to identify a joint line.

The joint line or lines may be estimated using an artificial intelligence procedure (e.g., a machine learning model), for example based on shape matching to determine healthy bone of a reference model. The joint lines estimated using this procedure may not be precise, and thus multiple joint lines may be displayed for a surgeon to select. A comparison of existing patient anatomy (e.g., femur or tibia, with or without implant) may be made to an atlas of x-ray data, in an example, to identify a likely joint line or lines.

In another example, a contra-lateral joint line may be determined (e.g., when a patient has one knee that does not have an implant, and another knee being planned for a revision having an implant). The joint line on the other knee (e.g., assuming there is no implant) may be used to estimate a joint line on the knee to undergo the revision.

In yet another example, landmark features may be used that are not typically used in generation of joint lines. These landmark features may be difficult for a person to identify. These landmark features may be identified by an AI model using labeled atlas images. In some examples, bone may be extrapolated (e.g., revealing landmarks that are more easily correlated to the joint line). In other examples, an AI model may use what is left of the tibia or the femur to determine the joint line based on remaining landmarks. Either technique may include generating a model of the bone or bones, and comparing the bone or bones to atlas bones to extract a model of the bones or the joint line. In some examples, where an implant may be identified (e.g., a size, a brand, a type, etc. of the implant), then that information may be used as calibration or for navigation to determine where landmarks would be in healthy bone, and thus determine a joint line.

The different joint lines 902, 904, 906 on example 900A may be selectable by a surgeon (e.g., displayed on a user interface) such that the surgeon may choose one for planning a revision procedure. Once selected, the joint line may be modified later, for example to select a different joint line or move the joint line manually. The different joint lines 902, 904, 906 may be identified using one technique, with different estimations based on a range of tolerance, in one example. For example, a median or average estimate may be identified and displayed as joint line 904. An error range may be identified for the median or average estimate, and joint lines 902 and 906 may be displayed based on the error range (e.g., at 25% and 75% of the error range, half way from the median or average estimate to an extreme of the error range, or at limits of the error range). Additional joint lines may be displayed as well, the display is not limited to three joint lines.

In another example, two joint lines (e.g., any two of 902, 904, and 906) may be generated using different techniques. For example, one of the joint lines may be determined by extrapolating bone using a comparison to a bone or bones an atlas, and determining a joint line from a closest extrapolation or a set of close bone extrapolations (which may include using a closest model directly, or extrapolating between or among models, which may include an extrapolation not directly represented in the atlas). Another technique may include using landmarks (e.g., using a robotic surgical device to determine difficult or non-typical landmarks, or extrapolating estimated landmarks from current data). Still another technique may include using a model (e.g., a machine learning or other AI model), based on previous data (e.g., a supervised learning technique model) to identify the joint lines. Joint line 908 may represent an average or median of multiple techniques.

Example view 900C of FIG. 9C includes additional details of a revision planning user interface. For example, in addition to the joint line 901, the example view 900C includes a reamer 916 with an end portion 918 and a current bone line 912. The current bone line 912 may be generated using preoperative imaging, estimation, or the like. In an example, the view 900C may be an intraoperative view, which may be used to modify a preoperative plan. In this example, the current bone line 912 may be identified using a camera, a robotic surgical device, via digitizing, or the like.

Additional detail is provided in the example view 900C, including augments 913 and 917. These augments may be generated based on a distance between a tibial surface 914 and the current bone line 912 or the end portion 918 of the reamer 916, for example.

The view 900C configuration may be used to illustrate how a femoral component augment may be determined. For example, a robotic surgical device may correlate canal and posterior condyles (e.g., at augments 917 and 913, respectively) with the tibial cut surface 914. The robotic surgical device may map the tibial surface 914 to the current bone line 912. The mapping may be used to determine an augment size. The robotic surgical device may include an end effector to digitize the tibial cut surface 914, and use an image-based model or further digitizing to determine a location of the current bone line 912. The augments 913 or 917 may be determined using a coordinate system of the robotic surgical device.

In an example, the tibial surface 914 may be prepared using a burr. A robotic surgical device may be used to automatically burr the tibia to generate the tibial surface 914, for example based on a preoperative or intraoperative plan indicating a cut depth. The plan may indicate a surface depth of the tibial surface 914, or may indicate an augment depth, and the robotic surgical device may automatically generate the tibial surface 914 by burring the tibia.

Figure 10:
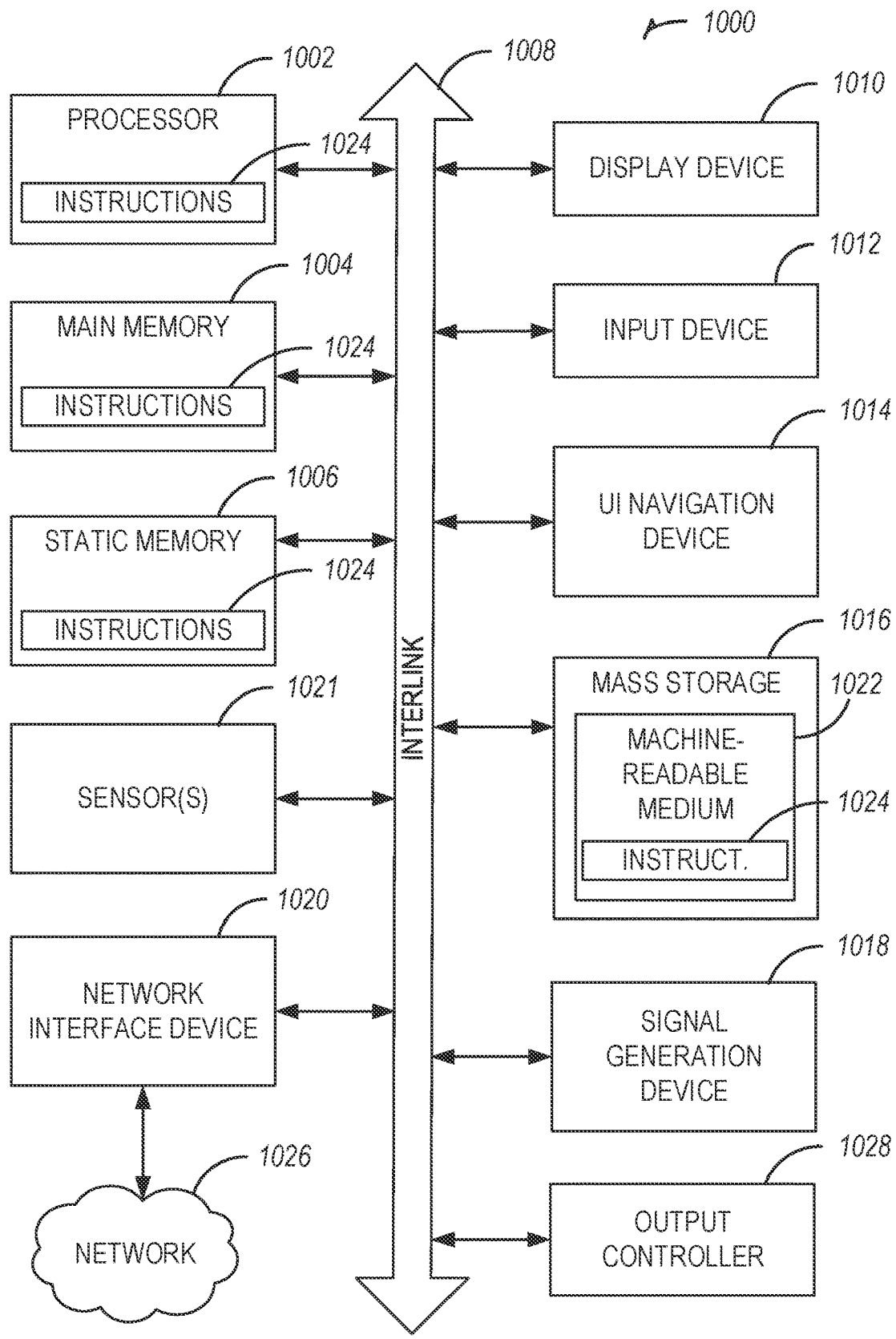
FIG. 10 illustrates a block diagram of an example machine upon which any one or more of the techniques discussed herein may perform in accordance with at least one example of this disclosure.

FIG. 10 illustrates a block diagram of an example machine 1000 upon which any one or more of the techniques discussed herein may perform in accordance with some embodiments. In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010, an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 may include an output controller 1028, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, and/or associated caches and servers) configured to store the one or more instructions 1024. The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine-readable medium examples may include solid-state memories, and optical and magnetic media.

The instructions 1024 may further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

Each of the following non-limiting examples may stand on its own, or may be combined in various permutations or combinations with one or more of the other examples.

Example 1 is a tensor device comprising: a femoral arm configured to couple with an end portion of a femoral intramedullary canal reamer; a tibial arm moveably connected to the femoral arm, the tibial arm configured to couple with an end portion of a tibial intramedullary canal reamer; and a slider component coupled at a first end to the femoral arm and coupled at a second end to the tibial arm, the slider component configured to move based on movement of the femoral arm with respect to the tibial arm and the slider component including an indicator to identify a knee gap.

In Example 2, the subject matter of Example 1 includes, wherein the tensor device further comprises a lock lever configured to lock the slider component to the identified knee gap.

In Example 3, the subject matter of Examples 1-2 includes, wherein the slider component further comprises a cut guide.

In Example 4, the subject matter of Examples 1-3 includes, wherein the tensor device includes a lock configured to be screwed to lock the femoral arm and the slider in fixed positions relative to the tibial arm.

In Example 5, the subject matter of Examples 1-4 includes, wherein the slider component further includes an offset dial configured to identify an offset of one of the femoral intramedullary canal reamer or the tibial intramedullary canal reamer.

Example 6 is a method of using a tensor device, the method comprising: receiving an indication including a joint line of a knee for a revision procedure; causing, using processing circuitry, a robotic arm to align a femoral arm of a tensor device parallel to an intramedullary axis of a tibia, according to the joint line, while a tibial arm of the tensor device is connected to an end portion of a tibial reamer; determining, using the processing circuitry, a component size for an implant based on the alignment of the femoral arm; and outputting the component size for display in a user interface.

In Example 7, the subject matter of Example 6 includes, receiving an adjustment to the joint line, and outputting an updated component size.

In Example 8, the subject matter of Examples 6-7 includes, wherein the implant is a femoral implant, and wherein outputting the component size includes outputting a recommended femoral cut.

In Example 9, the subject matter of Examples 6-8 includes, wherein the implant is a tibial implant, and wherein outputting the component size includes outputting a recommended tibial cut.

In Example 10, the subject matter of Examples 6-9 includes, wherein the user interface is part of a planning application, and wherein the indication is received on the user interface, via a surgeon selection.

In Example 11, the subject matter of Example 10 includes, digitizing a plurality of points on a knee of a patient, and outputting, for display, a 3D model of the patient knee on the user interface.

In Example 12, the subject matter of Examples 6-11 includes, controlling the robotic arm to position the arms of the tensor device to assess ligament balance in extension and determining whether ligaments are valid in flexion.

In Example 13, the subject matter of Examples 6-12 includes, wherein the component size corresponds to a knee gap corresponding to the alignment of the femoral arm.

In Example 14, the subject matter of Examples 6-13 includes, determining a femoral component offset using robotically determined canal and posterior condyles locations, a location of a tibial cut surface, and a ligament tension at extension.

In Example 15, the subject matter of Examples 6-14 includes, determining an augment based on known locations identified via the robotic arm and the joint line.

In Example 16, the subject matter of Examples 6-15 includes, outputting, for display in the user interface, varus or valgus values throughout a range of motion based on tension values identified throughout the range of motion.

Example 17 is a revision system comprising: a tensor device, including a femoral arm configured to couple with an end portion of a femoral intramedullary canal reamer, a tibial arm configured to couple with an end portion of a tibial intramedullary canal reamer, and a slider component configured to move based on movement of the femoral arm with respect to the tibial arm; a robotic surgical device including: a robotic arm; memory, including instructions, which when executed by processing circuitry, cause the processing circuitry to: cause the robotic arm to move the femoral arm parallel to an intramedullary axis of a tibia, according to a joint line; determine a component size for an implant or a knee gap based on the alignment of the femoral arm; and output the component size or the knee gap for display in a user interface.

In Example 18, the subject matter of Example 17 includes, wherein the tensor device further comprises a lock lever configured to lock the slider component to the identified knee gap.

In Example 19, the subject matter of Examples 17-18 includes, wherein the slider component further comprises a cut guide.

In Example 20, the subject matter of Examples 17-19 includes, wherein the tensor device includes a lock configured to be screwed via the robotic arm to lock the femoral arm and the slider in fixed positions relative to the tibial arm.

In Example 21, the subject matter of Examples 17-20 includes, wherein the processing circuitry is further caused to identify, using the robotic arm, an offset of one of the femoral intramedullary canal reamer or the tibial intramedullary canal reamer.

In Example 22, the subject matter of Examples 17-21 includes, wherein the processing circuitry is further caused to receive an adjustment to the joint line, and output an updated component size.

In Example 23, the subject matter of Examples 17-22 includes, wherein the implant is a femoral implant, and wherein outputting the component size includes outputting a recommended femoral cut.

In Example 24, the subject matter of Examples 17-23 includes, wherein the implant is a tibial implant, and wherein outputting the component size includes outputting a recommended tibial cut.

In Example 25, the subject matter of Examples 17-24 includes, wherein the user interface is part of a planning application, and wherein the indication is received on the user interface, via a surgeon selection.

In Example 26, the subject matter of Example 25 includes, wherein the processing circuitry is further caused to digitize a plurality of points on a knee of a patient, and output, for display, a 3D model of the patient knee on the user interface.

In Example 27, the subject matter of Examples 17-26 includes, wherein the processing circuitry is further caused to control the robotic arm to position the arms of the tensor device to assess ligament balance in extension and determine whether ligaments are valid in flexion.

In Example 28, the subject matter of Examples 17-27 includes, wherein the component size corresponds to a knee gap corresponding to the alignment of the femoral arm.

In Example 29, the subject matter of Examples 17-28 includes, wherein the processing circuitry is further caused to determine a femoral component offset using robotically determined canal and posterior condyles locations, a location of a tibial cut surface, and a ligament tension at extension.

In Example 30, the subject matter of Examples 17-29 includes, wherein the processing circuitry is further caused to determine an augment based on known locations identified via the robotic arm and the joint line.

In Example 31, the subject matter of Examples 17-30 includes, wherein the processing circuitry is further caused to output, for display in the user interface, varus or valgus values throughout a range of motion based on tension values identified throughout the range of motion.

Example 32 is at least one machine-readable medium including instructions that, when executed by processing circuitry, cause the processing circuitry to perform operations to implement of any of Examples 1-31.

Example 33 is an apparatus comprising means to implement of any of Examples 1-31.

Example 34 is a system to implement of any of Examples 1-31.

Example 35 is a method to implement of any of Examples 1-31. Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A tensor device comprising:
   a femoral arm configured to couple with an end portion of a femoral intramedullary canal reamer;
   a tibial arm moveably connected to the femoral arm, the tibial arm configured to couple with an end portion of a tibial intramedullary canal reamer; and
   a slider component having a first major surface and a second major surface, the slider component including:
      a first end including:
         an aperture extending from the first major surface to the second major surface, the aperture configured to movably attach the slider component to the femoral arm, the aperture encircling the femoral arm such that the femoral arm can move through the aperture;
      a second end coupled to the tibial arm, the slider component configured to move based on movement of the femoral arm with respect to the tibial arm caused by movement of a knee;
      a gap indicator to identify, via movement of the slider component relative to one or more of the femoral arm or the tibial arm, a knee gap of the knee; and
      an offset indicator surrounding the aperture to identify, via concentric misalignment of the femoral arm and the aperture, an offset of the femoral intramedullary canal reamer relative to a central axis of a femur.

2. The tensor device of claim 1, wherein the tensor device further comprises a lock lever configured to lock the slider component to the identified knee gap.

3. The tensor device of claim 1, wherein the slider component further comprises a cut guide.

4. The tensor device of claim 1, wherein the femoral arm being movably connected to the tibial arm forms a first connection between the femoral arm and the tibial arm and the slider component forms a second connection between the femoral arm and the tibial arm.

* * * * *